US012603160B2

(12) United States Patent
Brooks

(10) Patent No.: US 12,603,160 B2
(45) Date of Patent: Apr. 14, 2026

(54) SYSTEM AND METHOD FOR ASSESSING IMMUNE STATUS RELATED TO TRANSMISSIBLE INFECTIOUS DISEASES FOR MITIGATING AGAINST TRANSMISSION

(71) Applicant: Andrew Brooks, Los Angeles, CA (US)

(72) Inventor: Andrew Brooks, Los Angeles, CA (US)

( * ) Notice: Subject to any disclaimer, the term of this patent is extended or adjusted under 35 U.S.C. 154(b) by 409 days.

(21) Appl. No.: 17/540,674

(22) Filed: Dec. 2, 2021

(65) Prior Publication Data

US 2022/0254460 A1 Aug. 11, 2022

Related U.S. Application Data

(60) Provisional application No. 63/121,731, filed on Dec. 4, 2020.

(51) Int. Cl.
| | |
|---|---|
| *G06Q 50/00* | (2024.01) |
| *G06K 19/06* | (2006.01) |
| *G16H 10/60* | (2018.01) |
| *G16H 40/67* | (2018.01) |

(52) U.S. Cl.
CPC ....... *G16H 10/60* (2018.01); *G06K 19/06037* (2013.01); *G16H 40/67* (2018.01)

(58) Field of Classification Search
CPC ... G16H 10/60; G16H 40/67; G06K 19/06037
See application file for complete search history.

(56) References Cited

U.S. PATENT DOCUMENTS

| | | | | |
|---|---|---|---|---|
| 2020/0294634 A1* | 9/2020 | Katz | ...................... | G16H 50/30 |
| 2021/0052231 A1* | 2/2021 | Naga Sripada | ........ | A61B 5/746 |
| 2021/0313026 A1* | 10/2021 | Wagner | ................ | A61B 5/1176 |
| 2021/0326474 A1* | 10/2021 | Sparks | ................... | G06Q 10/10 |
| 2021/0335458 A1* | 10/2021 | McMullen | ........... | G06K 7/1095 |
| 2021/0343395 A1* | 11/2021 | Pan | ........................ | G16H 30/20 |
| 2021/0350649 A1* | 11/2021 | Jafri | ..................... | H04W 12/64 |
| 2023/0298416 A1* | 9/2023 | Luthra | ............. | G06K 19/06037 |
| | | | | 340/5.52 |

* cited by examiner

*Primary Examiner* — Rajesh Khattar
(74) *Attorney, Agent, or Firm* — Olivo IP Law Group P.C.; John W. Olivo, Jr.

(57) ABSTRACT

The invention relates to a solution for mitigating against transmitting, receiving or hosting transfers of infectious diseases through access to a user's health record via a mobile, cloud server-based application. The user's heath record data is stored in the application database, and can include immunization records, test results, and pre-existing conditions. This data is accessed using the mobile application interface by scanning a uniquely generated Quick Response (QR) code, and displayed through an application downloaded to a separate device, such as one owned by a venue. The user's code is scanned to display an immunity score and verified by the user's identification data, matched to data on the second device. This data can also be accessed by other users, such as venue owners who want to insure the health and safety of their patrons.

15 Claims, 13 Drawing Sheets

TrustedPatron PoC

TrustedPatron PoC

SYSTEM AND METHOD FOR ASSESSING IMMUNE STATUS RELATED TO TRANSMISSIBLE INFECTIOUS DISEASES FOR MITIGATING AGAINST TRANSMISSION

PRIORITY CLAIMS

This application claims the benefit of U.S. Provisional Application Ser. No. 63/121,731, filed Dec. 4, 2020, the contents of which are incorporated herein by reference.

BACKGROUND OF THE INVENTION

The exchange of electronic healthcare information over networks is increasing. Currently, the electronic healthcare information is exchanged between medical offices and other physicians, local hospitals and clinics, location and national labs and imaging centers, insurance payers, local pharmacies, public health and government agencies and patients. The need for instant personal access to one's health data is also an emerging need in the age of increased viral outbreaks and global pandemic situations.

Access to personal health records can involve coordinating care for patients in emergency situations. Streamlined access to health data advocates for a focus on preventive, comprehensive care to improve the health of the entire population. Due to the development of enhanced mobile internet access, advances can now be made in obtaining one's health record. In the past, doctors have been the repository of medical information and the ones to "arrange" it so that it had clinical meaning. But these functions can now be performed in an automated way using telecommunication and mobile technologies.

Medical data collection, storage and display systems of great variety in construction and purpose are often employed for medical and non-medical purposes. A feature common to such systems is a means for identifying a particular patient or client and the associated, relevant medical records. Human disease status is highly confidential information subject to misuse by any of a variety of agencies or individuals. Accordingly, it is desirable to provide reliable data on health and/or infectious status in an anonymous fashion whereby the person viewing the data has some assurance that the data correspond to the individual with whom they are considering carrying out such activities. However, this alone is not necessarily sufficient because it is desirable to be able to have access to the data on instant, on demand basis.

Users often face the challenge of storing important medical (and non-medical) documents in one central, secure location that may be readily accessed when needed, such as immunization records and pre-existing health conditions. Additionally, such important medical and non-medical information is invariably not accessible when it is needed most.

SUMMARY OF THE INVENTION

The present invention pertains to a solution for mitigating against transmitting, receiving or hosting transfers of infectious diseases through the use of instant access to a user's personal health record via a mobile, cloud server-based application. This data can also be accessed by other users, such as venue owners who want to insure the health and safety of their patrons.

In one embodiment of the present invention, the application can store all health record data for the user, including but not limited to immunization records, test results, and pre-existing conditions. Data can be uploaded by healthcare providers and testing labs.

In another embodiment of the present invention, each user's data is stored on a database, and can be accessed through a mobile application using a uniquely generated scan code or Quick Response (QR) code via the application interface. The user's unique code can also be accessed through an application downloaded to a separate device, such as one owned by a venue. The user's code is then processed and verified using the user's identification data, matched to data on the second device. Each user can also request health records such as lab data to be sent over and stored on the application database for the user's secure account.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

DETAILED DESCRIPTION OF THE PREFERRED EMBODIMENT

Figure 1:
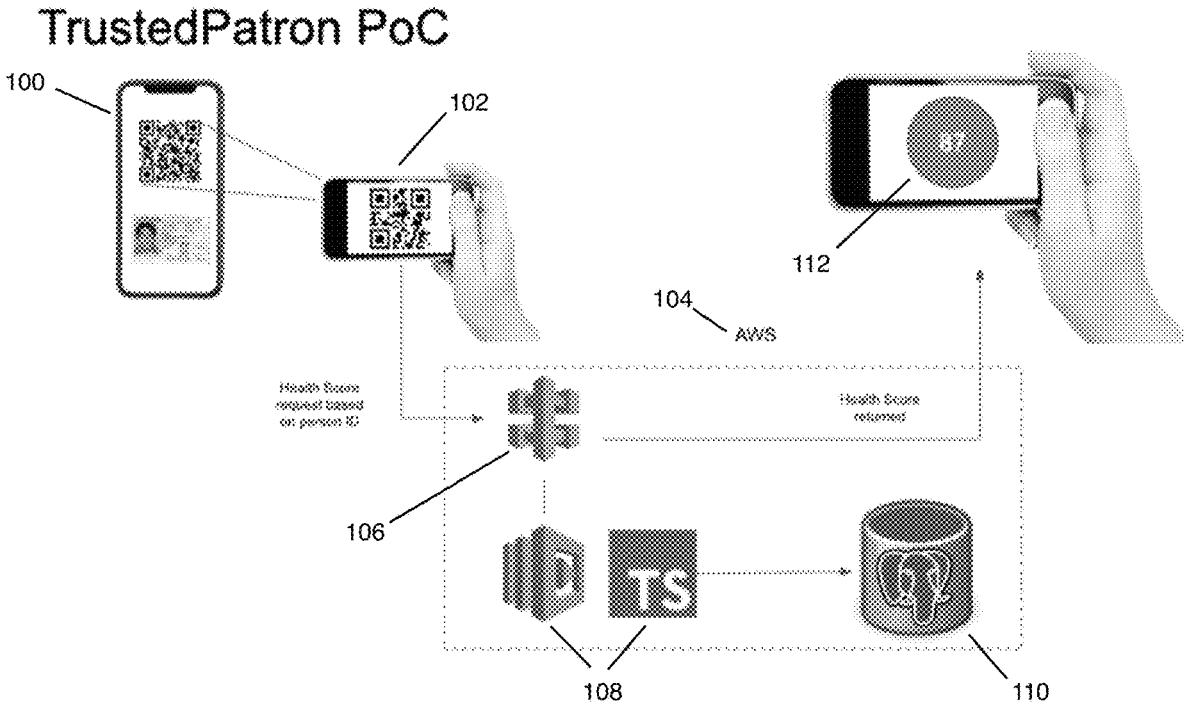
FIG. 1 is a diagram of the overall system of the present invention.

FIG. 1 is a diagram of the overall system of the present invention. In accordance with the preferred embodiment of the present invention, the user application can be accessed through an application on a mobile device 100. The user's unique QR code is scanned using a scanning feature on a separate mobile device 102, such as a mobile device used by a venue. Once the user's QR code is scanned 102, the user's data can be accessed from where it is stored on a cloud platform 104, such as Amazon Web Services (AWS). The data is accessed through an API gateway (106) and can then be processed through functions such as TypeScript and AWS Lambda 108, and saved to an open source relational database such as PostgreSQL 110. Once the scanned data has been accessed through the cloud platform 104, the health score of the individual is sent to the scanning user's mobile device 112.

Figure 2:
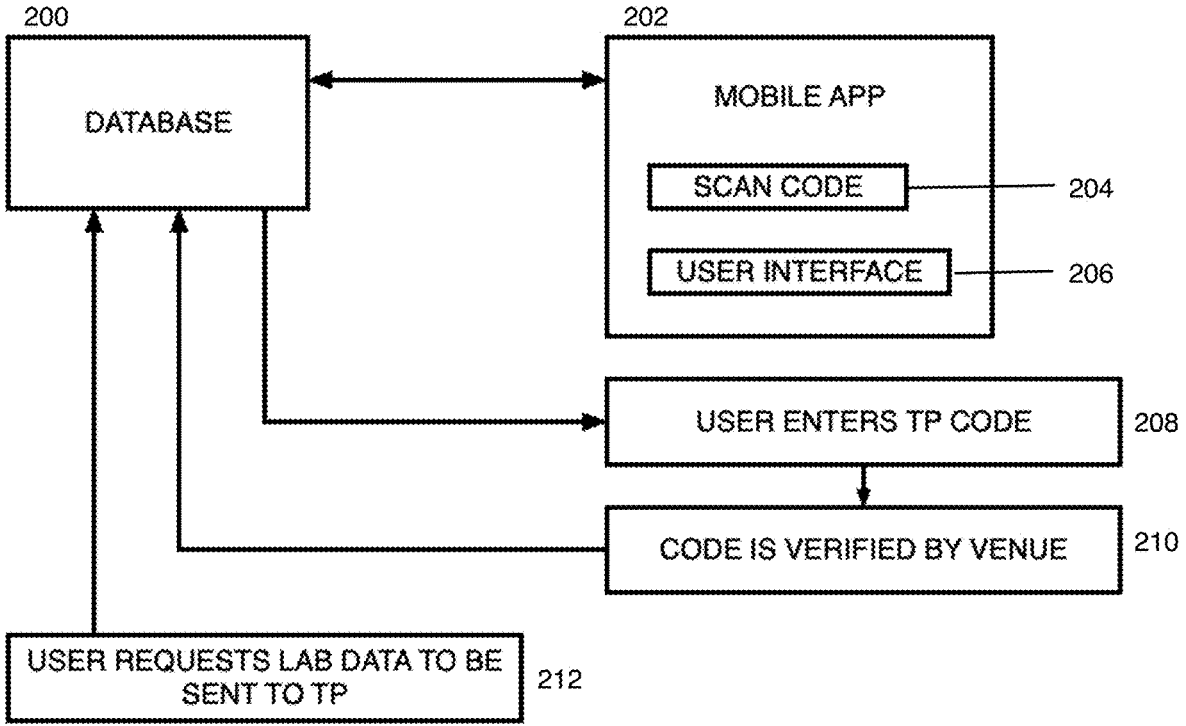
FIG. 2 is a process flow diagram of the present invention.

FIG. 2 is a process flow diagram of the present invention in use. In accordance with the preferred embodiment of the present invention, each user's data is stored on a database 200, and can be accessed through a mobile application 202 using a scan code 204 and a user interface 206. The user's unique code can also be entered into a separate device 208, such as one owned by a venue. The user's code is then processed and verified through the user's scanned code and identifying information by the secondary device, such as a device owned by a venue 210. Each user can also request health records such as lab data to be sent over and stored on the application database for the user's secure account 212.

Figure 3:
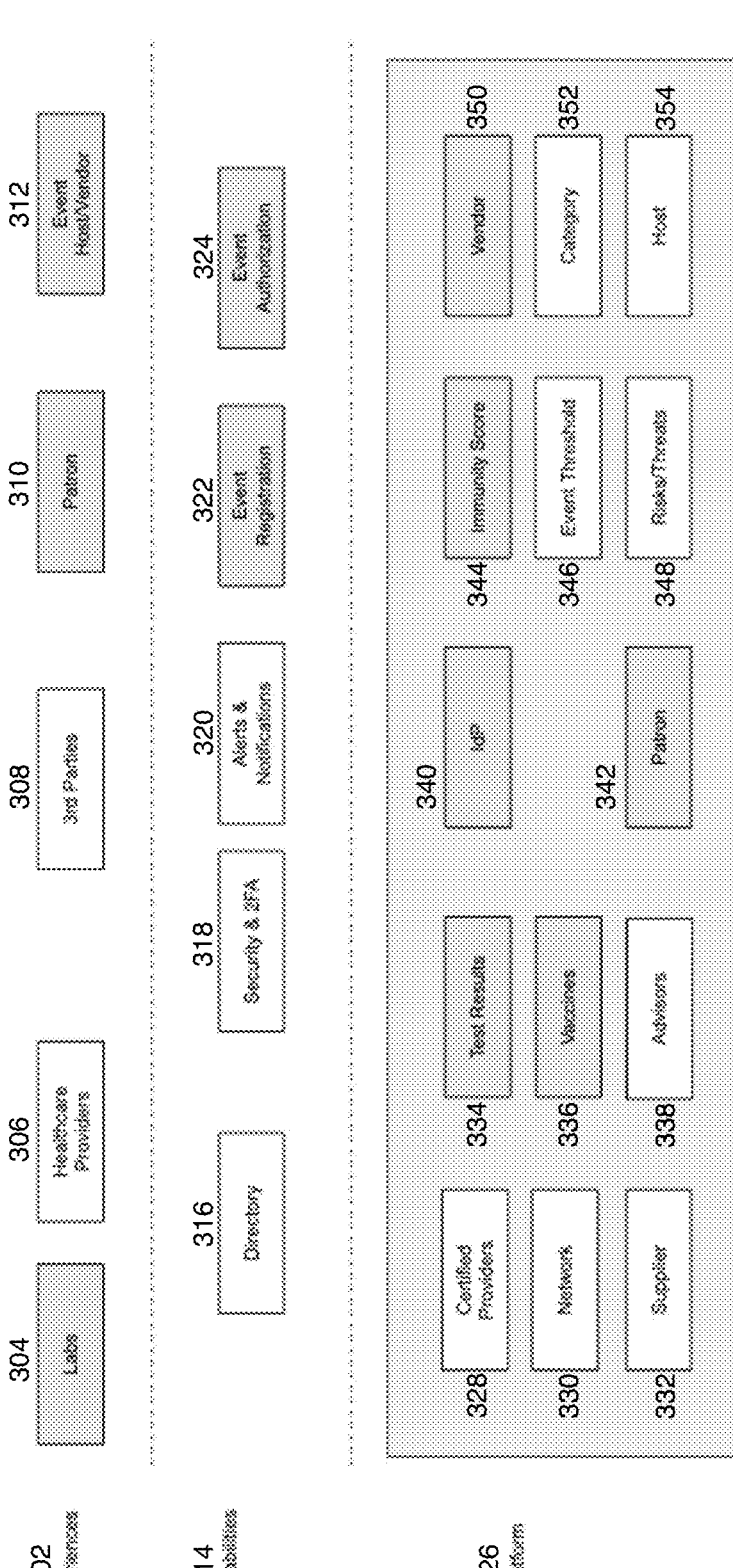
FIG. 3 is a diagram of the present invention domain model.

FIG. 3 is a diagram of the present invention domain model. In accordance with the preferred embodiment of the present invention, the domain model of the present invention is comprised of three categories: experiences 302; capabilities 314; and the application platform 326. The experiences 302 category includes user data provided by: labs 304; healthcare providers 306; third parties 308; the user or patron 310; and the event host, vendor or venue owner 312. The capabilities 314 category consists of modules such as: a directory 316; security and 2 factor authentication (2FA) 318; alerts and notifications 320; event registration 322; and event authorization 324. The platform 326 category is comprised of: certified providers 328; a network 330; suppliers 332; user test results 334 and vaccine history 336; health advisors 338; an identity provider system 340; the user or patron 342; the user's immunity or health score 344; an event threshold 346; user risks and threats 348; record of vendors or venues 350 that have previously accessed the user's data; a user category 352 and host information 354.

Figure 4:
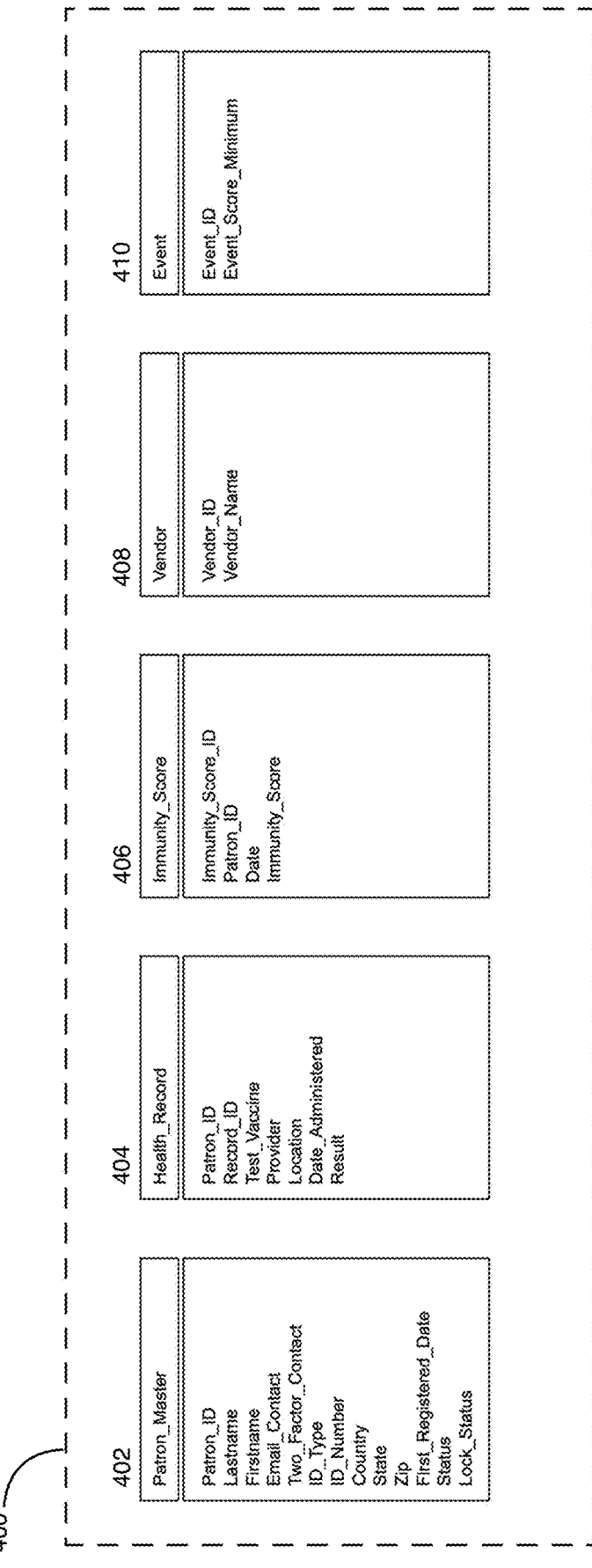
FIG. 4 is a diagram of the present invention processing framework.

FIG. 4 is a diagram of the present invention processing framework. In accordance with the preferred embodiment of the present invention, the processing framework 400 of the present invention is comprised of 5 modules. The Patron Master module 402 includes: patron identification data; first and last name; email; contact preferences; identification data type and identification data number; address information; registration date; patron status; and patron lock status. The Health Record module 404 includes: patron identification data; record identification data; test or vaccine data; the provider of the test or vaccine; the location of the test or vaccine; date of vaccination or test; and test results. The Immunity Score module 406 includes: immunity score identification data; patron identification data; the immunity score; and date that the score was calculated. The Vendor module 408 includes vendor identification data and the name of the vendor. The Event module 410 includes event identification data and the minimum event score.

Figure 5A:
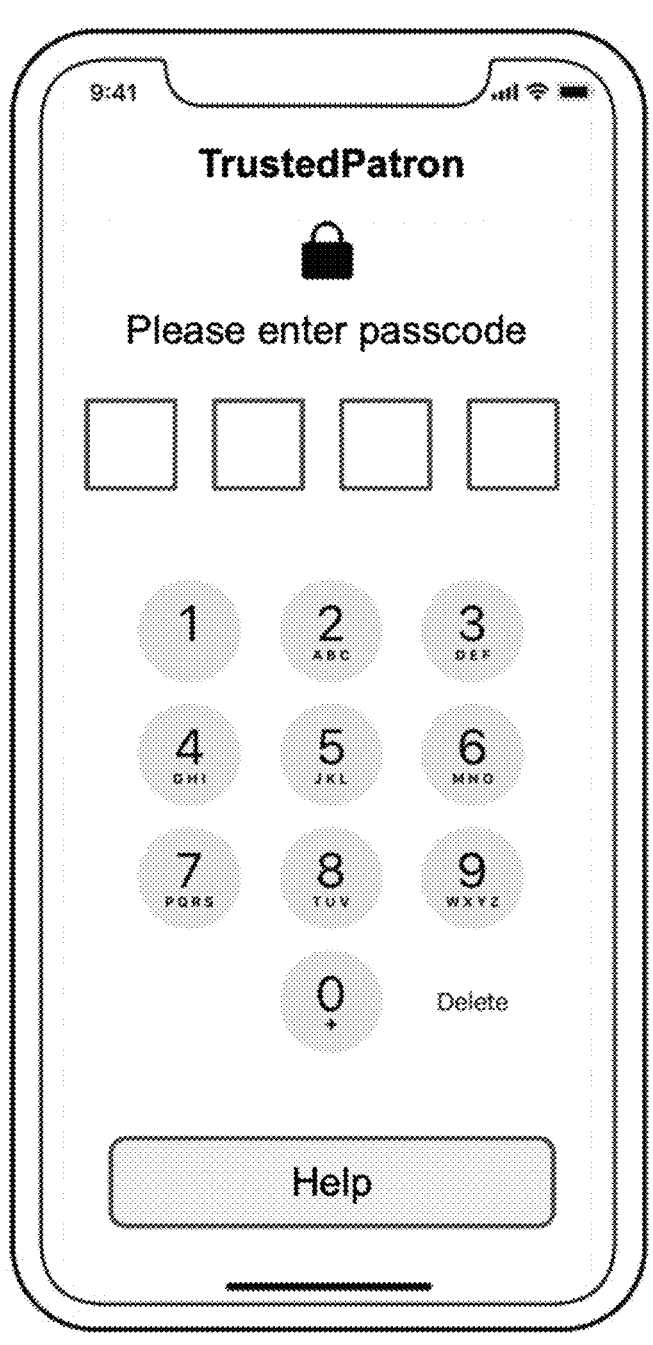
FIGS. 5A-5I are renderings of the mobile application interface of the present invention.
Figure 5B:
Figure 5C:
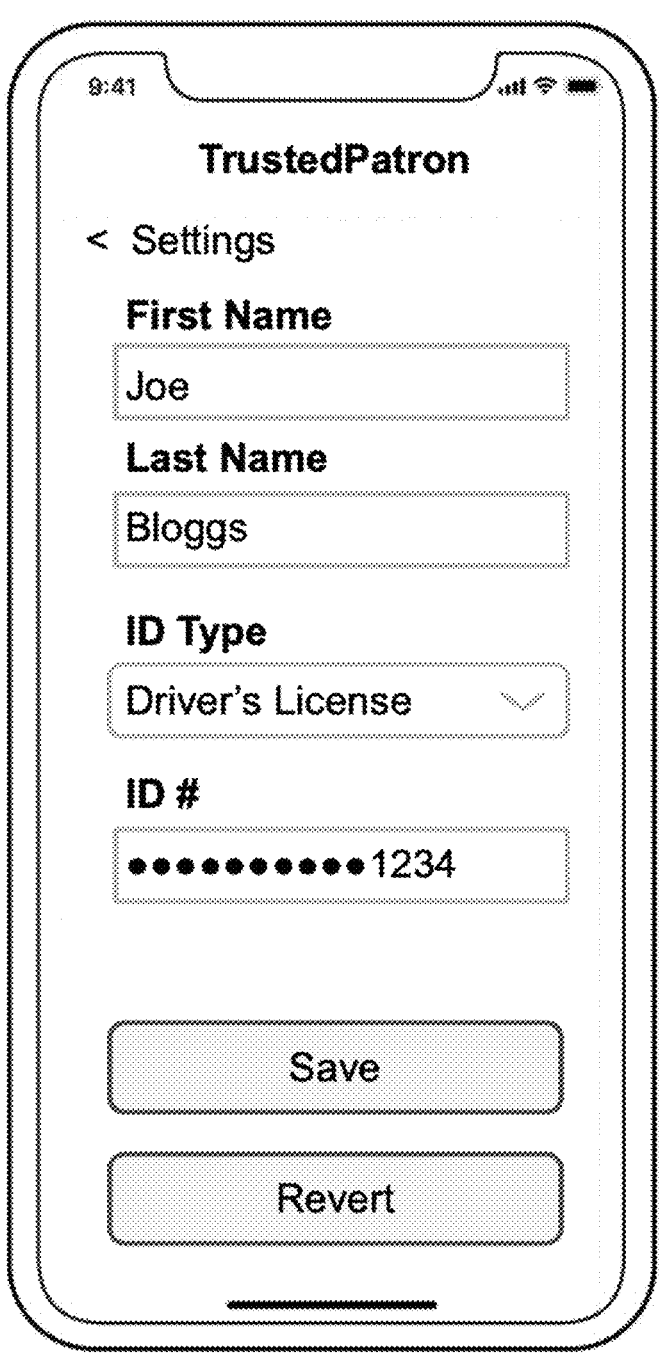
Figure 5D:
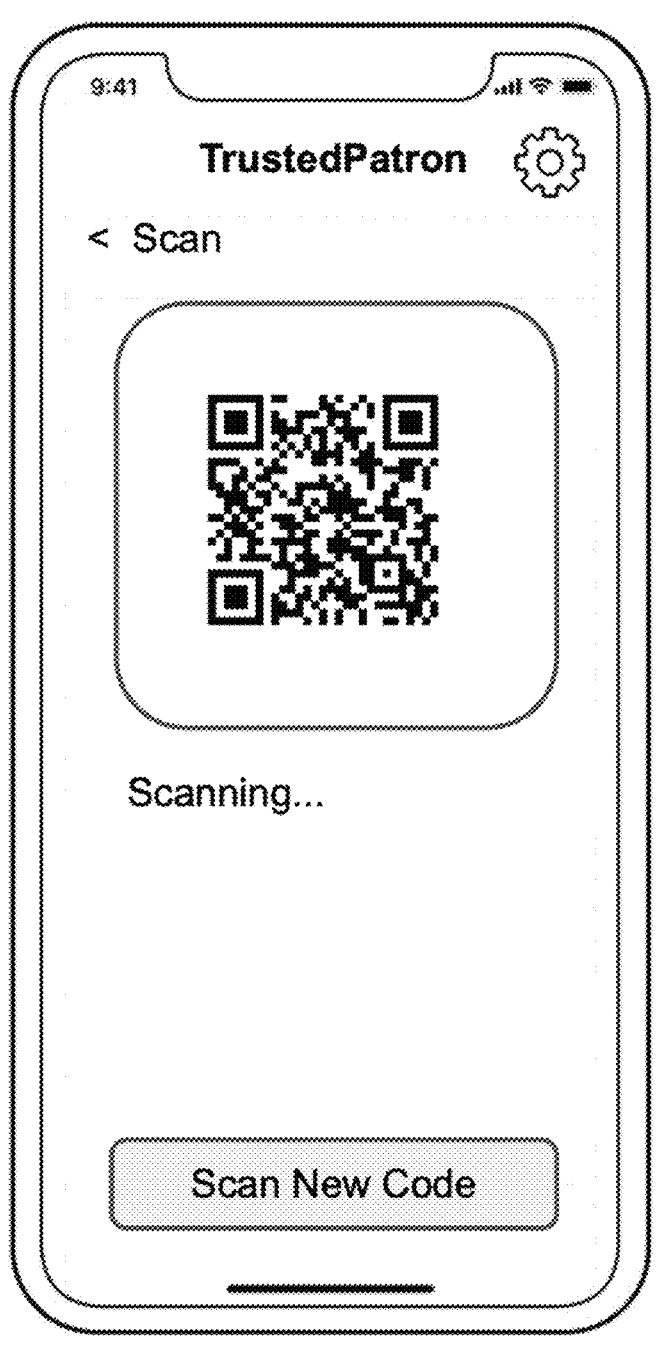
Figure 5E:
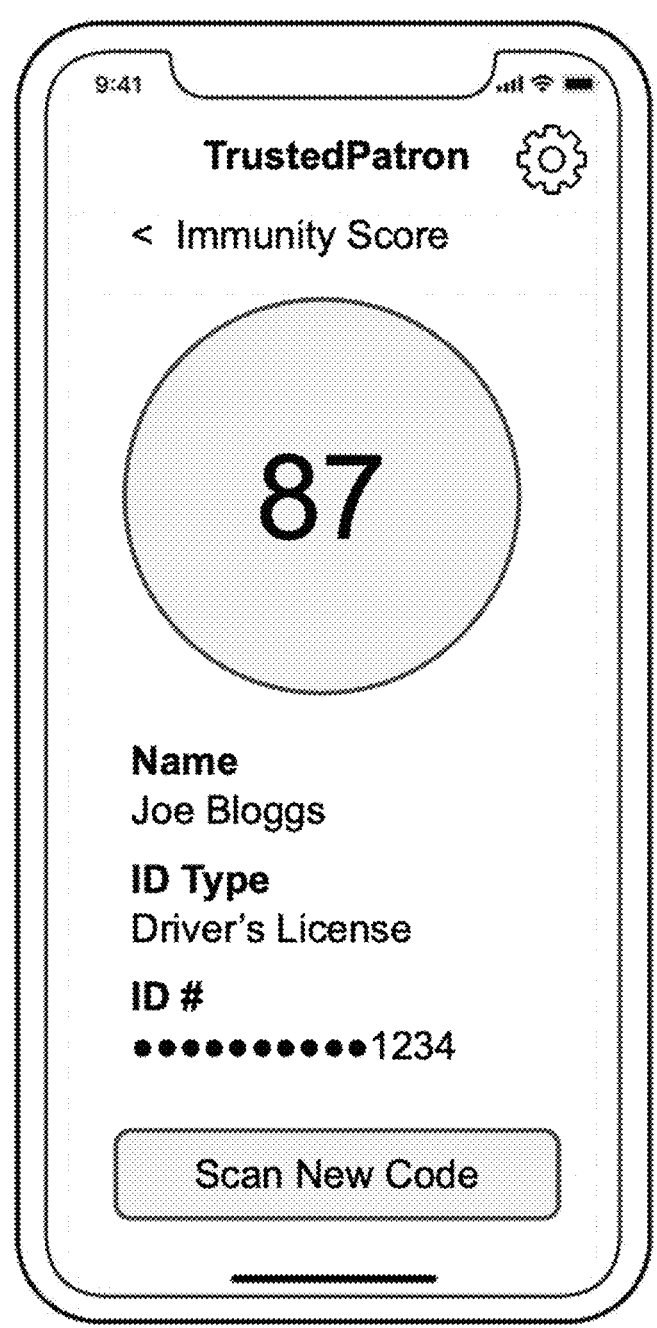
Figure 5F:
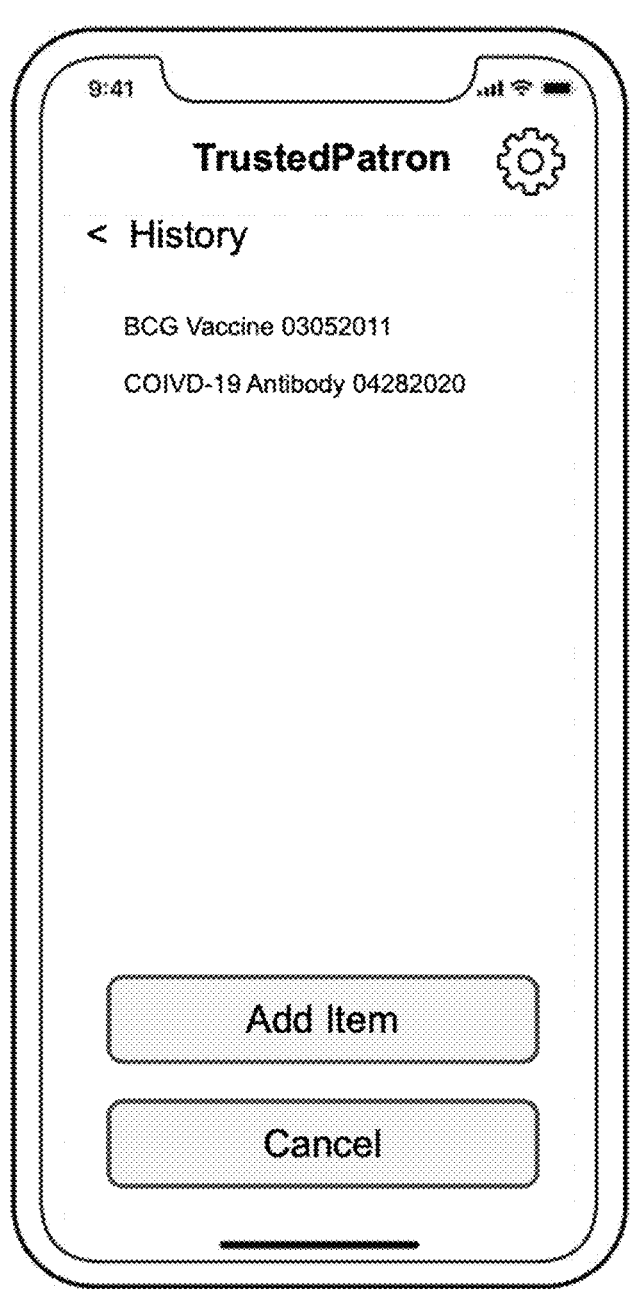

FIGS. 5A-5I are renderings of the mobile application interface of the present invention. FIG. 5A is a rendering of the user login screen of the mobile application, whereby the user must enter the user's passcode to access the application. FIG. 5B is a rendering of the main user screen that displays the name, identification (ID) type and number. This screen also displays a QR code uniquely generated for the user. When the QR code is scanned by the mobile application on another device, this allows for that device to access to the user's immunity score data. FIG. 5C is a rendering of the user settings screen, whereby user data including the name, ID type and ID number can be edited and saved or reverted to prior data. FIG. 5D is a rendering of the QR code scanning screen, signifying that a scan of the user's QR code is in process. FIG. 5E is a rendering of the user immunity score screen, displaying the user's current immunity score. The user's name, ID type and ID number are displayed underneath the immunity score for verification. FIG. 5F is a rendering of the immunity history data screen, wherein the user's test and vaccination data is displayed, including the name and date of each item. New entries can be added by selecting the add item option.

Figure 5G:
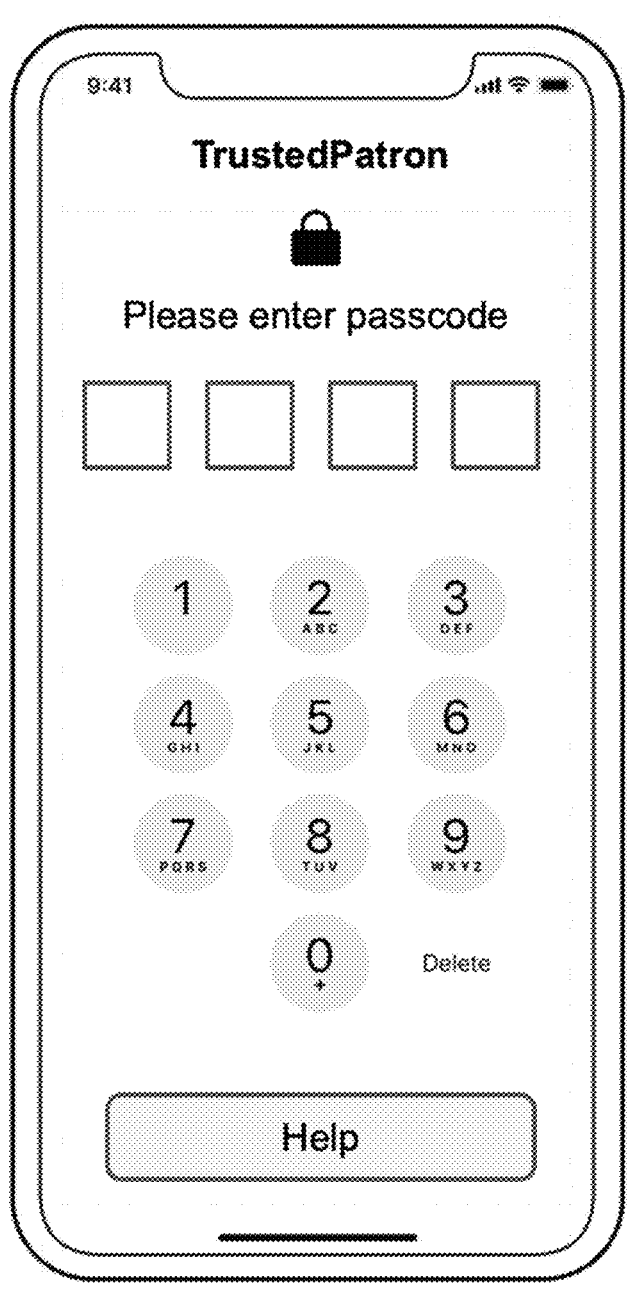
Figure 5H:
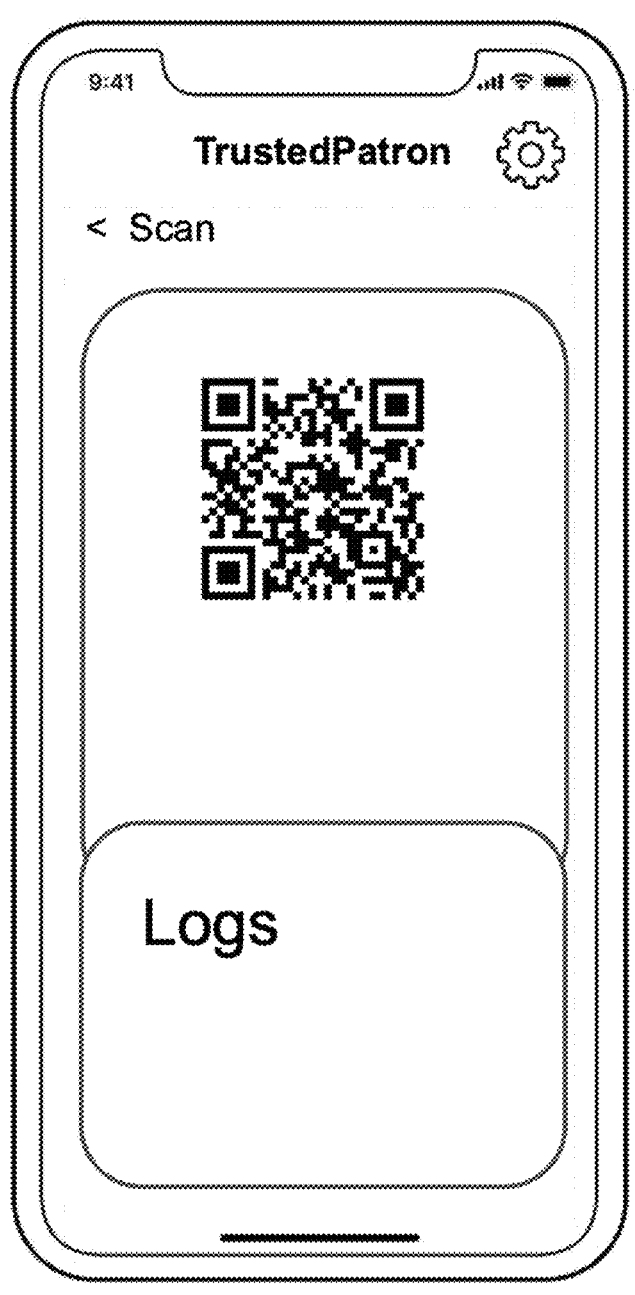
Figure 5I:
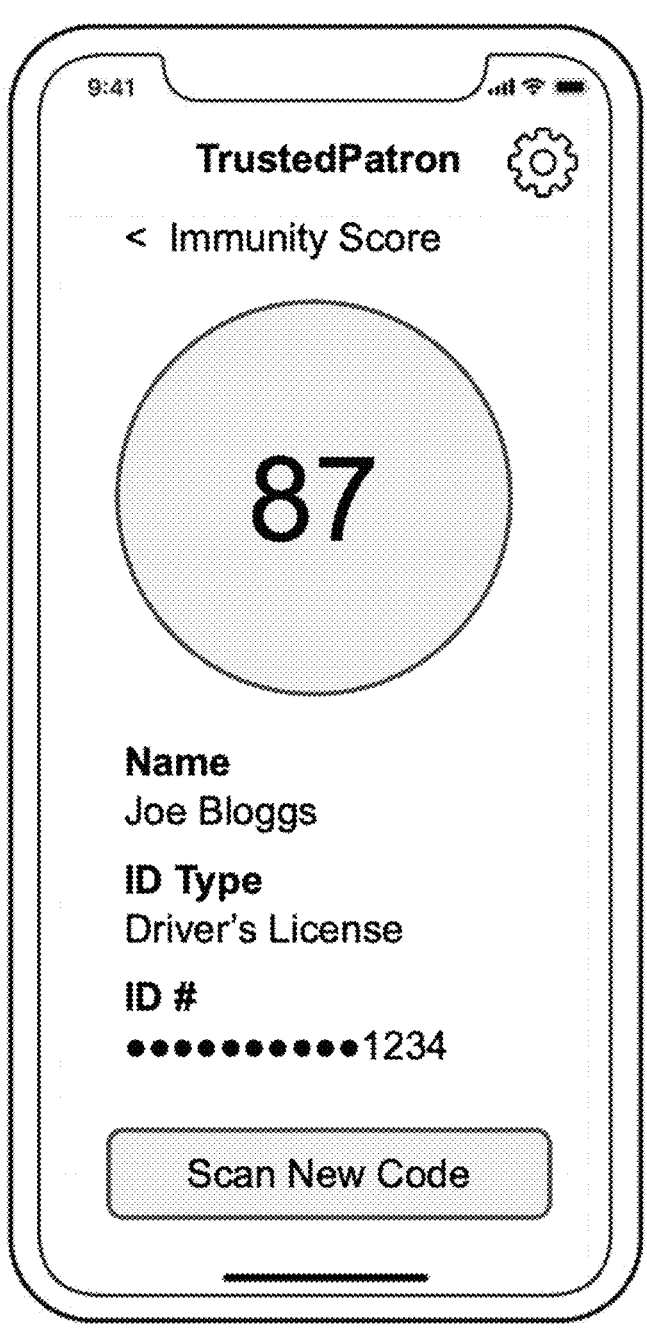

FIG. 5G is a rendering of the login screen for the vendor mobile application, whereby the user must enter the vendor's passcode to access the application. FIG. 5H is a rendering of the vendor scanning interface screen. Here, the vendor can initiate a new scan and access logged data of previous scans. FIG. 5I is a rendering of the vendor immunity score screen, displaying a scanned user's current immunity score.

The scanned user's name, ID type and ID number are displayed underneath the immunity score for verification. A new scan can also be initiated by selecting the scan new code option.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that may be included in the disclosed technology. The disclosed technology is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the technology disclosed herein. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, block diagrams and their accompanying description should not be construed as mandating a particular architecture or configuration.

What is claimed is:

1. A system for providing patron medical data to a host facility comprising:

A smartphone under control of said patron for interaction with said host facility, wherein said smartphone is connected with a cloud data server;

a screen of said smartphone configured to generate a unique QR code indicative of said patron medical including infectious disease and medical history associated with said patron and displaying said QR code upon said screen of said smartphone;

an immunity score software module configured to calculate a score based on said infectious disease and medical history including dates of infection and dates upon when said patron is less likely to infect fellow patrons, wherein said score is calculated using said patron's infectious disease history, including test and vaccination dates, to assess temporal risk of infection spread;

a patron master software module configured to collect patron identification data, wherein said patron identification data comprises a patron first and last name, a patron contact information and contact preferences, and a patron status;

a health record software module configured to store record identification data, including vaccine data and test data, wherein said records are stored in a relational database and are accessed via a cloud API gateway that enables access to health record data from the relational database and makes such data available for score computation and event assessment, said access being triggered upon QR code scan by a venue system;

a vendor software module configured to store vendor identification data;

an event software module configured to store event identification data and maintain a record of venues or vendors that previously accessed user data and associated risks, tracking user risks and threats related to a health event;

a host device configured to scan said unique QR code which, upon scanning, provides said score to said host facility so that a decision may be made whether to admit said patron into said host facility, wherein access to said QR code and health data is restricted via a security module implementing multi-factor authentication, including identity verification via authentication systems such as identity provider systems and vendor-specific password protection;

an application database configured to receive and store health records requested by said patron; and a password-protected application, storing thereupon data related to a vendor and accessible by a user via input of a vender-specific password;

a directory interface presented on said smartphone and connected to a patron's network and list of certified medical providers, wherein said smartphone includes said security module for implementing two-factor authentication, which authenticates the patron prior to enabling QR code generation and sharing of score data with external venue systems.

2. A system according to claim 1 wherein immunization medical data is included within said calculated score and is forwarded to a cloud database.

3. A system according to claim 1 wherein said infectious disease history includes medical data associated with airborne transmissible diseases and historical vaccination data.

4. A system according to claim 1 wherein said patron medical data includes data gathered and maintained by a professional medical services provider associated with said patron.

5. A system according to claim 1 wherein said patron medical data is encrypted and verified by way of two-factor authentication on a patron's communication device or personal account.

6. A method for providing patron medical data to a host facility comprising:

using a smartphone under control of said patron for interaction with said host facility, wherein said smartphone is connected with a cloud data server;

generating a unique QR code indicative of said patron medical including infectious disease and medical history associated with said patron and displaying said QR code upon a screen of said smartphone;

calculating, via an immunity score software module, a score based on said infectious disease and medical history including dates of infection and dates upon when said patron is less likely to infect fellow patrons, wherein said score is computed using retrieval of test and vaccine data from a cloud-based relational database via a secure API gateway, wherein said API enables secure access to said health record data by the immunity score module and event module;

providing a password-protected application and storing thereupon data related to a vendor and accessible by a user via input of a vender-specific password;

providing said score to said host facility and scanning user so that a decision may be made whether to admit said patron into said host facility, wherein said QR code is associated with stored identification data used to verify the patron's identity before health score data is accessed;

collecting, via a patron master software module, patron identification data, wherein said patron identification data comprises a patron first and last name, a patron contact information and contact preferences, and a patron status;

storing, via a health record software module, record identification data, including vaccine data and test data;

storing, via a vendor software module, vendor identification data;

storing, via an event software module, event identification data, and retrieving prior venue access and risk-related data via a platform component in communication with said event module upon QR code scan;

storing, in an application database, health records requested by said patron; and presenting a directory interface configured to a patron's network and list of certified medical providers, wherein said patron is verified via multi-factor authentication methods including identity provider systems before any QR code is generated and before score data is retrieved from the health record module and displayed.

7. A method according to claim 6 wherein immunization medical data is included within said calculated score and is forwarded to a cloud database.

8. A method according to claim 6 wherein said infectious disease history includes medical data and historical vaccination data associated with airborne transmissible diseases.

9. A method according to claim 6 wherein said patron medical data includes data gathered and maintained by a professional medical services provider associated with said patron.

10. A method according to claim 6 wherein said patron medical data is encrypted and verified by way of two-factor authentication on a patron's communication device or personal account.

11. A system for providing patron medical data to a host facility comprising:

a smartphone under control of said patron for interaction with said host facility, wherein said smartphone is connected with a cloud data server;

a screen of said smartphone configured to generate a unique QR code indicative of patron medical history, including infectious disease history associated with said patron and displaying said QR code upon said screen of said smartphone;

a password-protected application, storing thereupon data related to a vendor and accessible by a user via input of a vender-specific password;

an immunity score software module configured to calculate a score on an immunity score module based on said infectious disease history and said medical history including dates of infection and dates upon when said patron is less likely to infect fellow patrons, wherein said score is calculated using patron's medical history, and the QR code is generated to uniquely identify the patron and the time of generation;

a patron master software module configured to collect patron identification data, wherein said patron identification data comprises a patron first and last name, a patron contact information and contact preferences, and a patron status;

a health record software module configured to store record identification data, including vaccine data and test data, wherein said API enables secure transfer of health record data from relational database and routes said data to the immunity score module and event module upon QR code scan by a venue system;

a vendor software module configured to store vendor identification data;

an event software module configured to store event identification data, and wherein said event module is configured to maintain a record of venues or vendors that previously accessed user data and related risks;

an application database configured to receive and store health records requested by said patron; and a host device configured to scan said unique QR code which, upon scanning, triggers retrieval of the health score and associated risk data from the cloud database, transferred through a secure API gateway to the venue system following identity verification, and wherein said score is then provided provides said score to said host facility so that a decision may be made whether to admit said patron into said host facility, and wherein said system comprises capabilities including a directory, security and two-factor authentication, alerts and notifications, event registration and event authorization, wherein identity verification is used to validate that said QR code belongs to the correct patron, and the application restricts health score access until the patron identity is verified via the security module.

12. The system of claim 11 further comprising certified providers, a physicians and patrons network, suppliers, user test results and vaccine history, for informing health advisors as to said patron's health score.

13. The system of claim 11 wherein a health threshold is set for an event to be conducted at said host facility and said patron may view said host facility that has accessed their health data.

14. The system of claim 11 wherein biometric identification verifies that said QR code is actually attributable to said patron.

15. The system of claim 11 with an interface with social media for providing information about host facility records to the public.

\* \* \* \* \*